United States Patent
Di Pierro

(10) Patent No.: US 7,374,748 B2
(45) Date of Patent: May 20, 2008

(54) PHARMACEUTICAL AND COSMETIC COMPOSITIONS FOR THE PROTECTION OF THE SKIN FROM DAMAGES INDUCED BY SUN RADIATIONS

(75) Inventor: Francesco Di Pierro, Milan (IT)

(73) Assignee: Indena S.p.A., Milan (IT)

( * ) Notice: Subject to any disclaimer, the term of this patent is extended or adjusted under 35 U.S.C. 154(b) by 291 days.

(21) Appl. No.: 10/469,300

(22) PCT Filed: Feb. 26, 2002

(86) PCT No.: PCT/EP02/02027

§ 371 (c)(1),
(2), (4) Date: Jan. 9, 2004

(87) PCT Pub. No.: WO02/072051

PCT Pub. Date: Sep. 19, 2002

(65) Prior Publication Data

US 2004/0115141 A1    Jun. 17, 2004

(30) Foreign Application Priority Data

Mar. 2, 2001    (IT) ............................ MI2001A0429

(51) Int. Cl.
*A61K 8/00* (2006.01)
*A61K 65/00* (2006.01)

(52) U.S. Cl. .......................... 424/59; 424/757; 424/764; 424/766

(58) Field of Classification Search ................. 424/725
See application file for complete search history.

(56) References Cited

U.S. PATENT DOCUMENTS

| 4,764,508 A | 8/1988 | Gabetta et al. |
| 4,963,527 A | 10/1990 | Bombardelli et al. |
| 6,147,054 A * | 11/2000 | De Paoli Ambrosi ......... 514/23 |

FOREIGN PATENT DOCUMENTS

| EP | 0 283 713 | 9/1988 |
| EP | 0 552 439 | 7/1993 |
| EP | 1 072 254 | 1/2001 |
| WO | WO 00/64472 | 11/2000 |

* cited by examiner

*Primary Examiner*—Christopher R Tate
*Assistant Examiner*—Randall Winston
(74) *Attorney, Agent, or Firm*—Young & Thompson

(57) ABSTRACT

Pharmaceutical and cosmetic compositions for the protection of the skin from damages induced by sun radiations, containing ingredients of vegetable origin, in addition to conventional sun filters and excipients.

7 Claims, No Drawings

PHARMACEUTICAL AND COSMETIC COMPOSITIONS FOR THE PROTECTION OF THE SKIN FROM DAMAGES INDUCED BY SUN RADIATIONS

The present invention relates to pharmaceutical and cosmetic compositions for the protection of the skin from damages induced by sun radiations, containing ingredients of vegetable origin, in addition to conventional sun filters and excipients.

More particularly, the present invention relates to pharmaceutical and cosmetics compositions for the protection of the skin from damages induced by sun radiations, containing phospholipid complexes of flavanolignanes extracted from *Silybum marianum*; phospholipid complexes of *Vitis vinifera* standardized extract and phospholipid complexes of triterpenes extracted from *Glycyrrhiza glabra*, in addition to conventional sun filters and excipients.

The formulation of preparations containing high-protection, specific sun filters has been one of the leading sectors of dermocosmetic research. This is due to the increasing market demand on the ground of both an ever increasing awareness of the public of the harmful effects of sun radiations and to the problem of the reduction of the ozone levels in the atmosphere.

Research in this field has allowed the formulation of diversified preparations, depending on the needs: products for intense exposure to sunlight (for example at the sea or in the mountains), for daily use (anti-aging) or for special uses, as is the case with exposure to UV rays for occupational reasons or in diseases of the pigmentary system (albinism, vitiligo).

Furthermore, there has recently been growth in the knowledge of the molecular mechanisms responsible for the consequences of the lack of protection from sunlight. This allows the formulation of preparations capable of opposing, at any level, the serious consequences which may be caused by non-protected exposure to sunlight.

As it is well known, long exposure to sunlight, as well as to ultraviolet radiations, may cause dermatological disorders, even to a serious degree.

The non-ionizing electromagnetic radiation of the UV spectrum makes up the sun emission portion which is today recognized as the main cause of skin alteration. The UV radiations which reach the earth's surface are UV-A (320 to 400 nm) and the UV-B (290 to 320 nm).

Disorders induced by UV radiations are herein generally referred to as "photodermatosis".

Mediated (toxic or allergic reactions to sunlight) and idiopathic (urticaria solaris, polymorphic dermatitis, actinic reticuloid) photodermatosis, as well as those liable to be worsened by sunlight (pellagra, lupus erythematosus, pemphigus erythematosus, xeroderma pigmentosum, dermatomyositis) may be considered as somewhat rare consequences of exposure to light. Conversely, direct photodermatosis is by far more frequent.

Photodermatosis may appear as erythema/edema vesiculosum reaction (acute damage), photo-aging and photo-carcinogenesis (chronic damage).

Erythema

Erythema is the most frequent skin reaction to UV radiation. It is dose-dependent and may range from modest, asymptomatic skin reddening to serious erythema which may be accompanied by pain, edema and the formation of vesicles. Erythema results from a peripheral capillary vasodilatation and is the consequence of both a direct interaction with blood vessels and a photochemical reaction triggered by sunrays on tissue chromophores (aromatic amino acids, nitrogenous bases, unsaturated fatty acids, etc.). A number of mediators are apparently involved in these interactions: prostaglandins of the E and D series, interleukins and mainly free radicals. The latter are released as a consequence of the energy transferred from chromophores to molecular oxygen, and are responsible for most of the vascular damage caused by exposure to sunlight.

Photo-aging

Skin aging is a complex biological process affecting various skin layers, including dermis. The aging process of those skin areas that are exposed to atmospheric agents is due, in addition to the so-called innate or intrinsic aging, namely the irreversible, degenerative process connected with aging which affects both the skin and internal organs, also to the extrinsic or photo-determined aging, which is mainly linked to ultraviolet exposure.

According to recent investigations, 80% of total damage in the areas exposed to atmospheric agents is determined by exposure to sunlight. From a cosmetic and pharmaceutical point of view, however, it is clear that action can be taken only against the second type of aging.

The above mentioned genesis of oxygen free radicals in turn promotes oxidative stress which damages such tissutal structures as endothelial membranes, proteins, nucleic acids and connective fibers. The consequences are:
excessive microcirculation permeability, which causes tissue hypoxia and edema;
protein denaturization, which is particularly dangerous in the case of structural proteins and enzymes;
lipidic peroxidation, which leads to cell death;
connective sclerosis.

A further damage induced by UV radiation is an increase in the transcription and translation processes of a particular DNA segment encoding for some metalloproteins exerting an effective digestive activity on collagen. This occurs at a speed markedly higher than that of reparative processes that act on the connective matrices, resulting in skin damage and the appearance of wrinkles.

Photo-carcinogenesis

Epidemiologic and clinical evidence has now demonstrated how deeply sun radiations, an in particular UV radiation, are involved in the development of some precancerous conditions (actinic keratoses) which may evolve into neoplastic lesions, such as basal cell epithelioma, spinocellular epithelioma and melanoma, which is the most dangerous.

So far, three are the mechanisms apparently involved in the development of neoplasms caused by UV radiation: mutation induced by the direct interaction with nitrogenous bases, interaction between free radicals and DNA, and UV-mediated immunosuppressiol induced at the skin level on the key cells in the immune response, namely dendritic cells, which are no longer capable of exerting an effective immune response that could suppress tumoral lesion.

In conclusion, it is clear that a tool aimed at providing a complete protection of the skin against any UV-mediated damage should be able to filter UV radiation, as well as act against oxidative stress, digestion of the connective tissue mucopolysaccharide fibers, mutagenic activity and UV-mediated immunosuppression. However, the preparations at present marketed do not meet all of the above cited requirements.

The present invention meets the above indicated requirements, providing pharmaceutical and cosmetic compositions which, in addition to conventional sun filters and excipients, also contain at least two of the following ingredients of vegetable origin:

| | | |
|---|---|---|
| a) | phospholipid complexes of flavanolignanes extracted from *Silybum marianum* | 0.1–5% |
| b) | phospholipid complexes of standardized extract of *Vitis vinifera* | 0.1–5% |
| c) | phospholipid complexes of triterpenes extracted from *Glycyrrhiza glabra* | 0.1–5% |

The pharmaceutical and cosmetic compositions of the present invention preferably contain at least two of the following ingredients of vegetable origin in the following percentages:

| | | |
|---|---|---|
| a) | phospholipid complexes of flavanolignanes extracted from *Silybum marianum* | 0.5% |
| b) | phospholipid complexes of standardized extract of *Vitis vinifera* | 1.5% |
| c) | phospholipid complexes of triterpenes extracted from *Glycyrrhiza glabra* | 1.5% | in combination with conventional sun filters and excipients.

The phospholipid complexes of flavanolignanes extracted from *Silybum marianum* (also referred to as "components a") are disclosed in EP 0.209.038.

They are characterized by excellent antioxidizing and antiinflammatory properties. In tests using $CCl_4$ as a pro-oxidant stimulus and hepatic microsomes as the target, the LC50 (micrograms per ml) of components a) corresponds to 25.0, while that of vitamin E (as the reference compound) is 30.0. As far as the antiinflammatory activity is concerned, components a) proved capable of inhibiting by 75% edema induced in the experimental animal paw through inoculation of croton oil. In man, components a), tested in 20 healthy volunteers against placebo, proved capable of inhibiting by 25% the erythematous reaction produced by skin exposure to ultraviolet radiation.

The phospholipid complexes of standardized extract of *Vitis vinifera* (also referred to as "components b") are disclosed in EP 0.275.224.

In-vitro assays demonstrated the extremely powerful anti-oxidant activity of components b). In tests using $Fe^{+++}$/ADP as a stimulus and liposomial preparations as the target of oxidation, components b) proved to be 35 times more active than catechin and 50 times more active than vitamin E. It should also be underlined that these complexes inhibit by 95% lipidic peroxidation induced by ultraviolet radiation, even at concentrations as low as 10 micromoles.

Components b) also proved to be able to inhibit, though in a non-competitive way, any elastase, collagenase and hyaluronidase present in inflamed tissue: this characteristic is extremely useful for a product developed to contrast skin photo-aging.

In recent mutagenesis assays, components b) showed excellent anti-mutagenic properties. Tests on spontaneous mutation of *Saccharomyces cerevisiae* (yeast and eukaryotic cells) demonstrated that these complexes can reverse mutation of the mitochondrial and nuclear DNA by 60% and 90%, respectively (0.5 mg/ml).

The anti-immunosuppressive properties of components b) were also evaluated. Components b), applied topically on the skin of nude mice and tested against placebo, inhibit UV-mediated skin immunosuppression by about 50%. In man, test in 18 healthy volunteers showed an 30% inhibition of the erythematous reaction produced by skin exposure to ultraviolet radiation.

The phospholipid complexes of triterpenes extracted from *Glycyrrhiza glabra* (also referred to as "components c") are disclosed in EP 0.283.713.

They exert powerful anti-inflammatory action upon topical administration, inhibiting the conversion of cortisol from its active to inactive form through inhibition of tissular 11-beta hydroxysteroidehydrogenese, extending the anti-inflammatory action of cortisol released following an inflammatory stimulus. Components c) proved capable of inhibiting by 95% the edema induced in the experimental animal paw through inoculation of croton oil, showing greater effectiveness than common non-steroidal anti-inflammatories (in this case indomethacin).

Components a), b) and c) were also toxicologically tested. The results of the acute toxicity tests carried out in the rat are summarized in the following Table.

| Component | oral LD50 mg/kg | intraperitoneal LD50 mg/kg |
|---|---|---|
| a) | >3.000 | >2.000 |
| b) | >5.000 | >2.221 |
| c) | >2.000 | >4.432 |

Furthermore, acute and chronic cutaneous irritation tests in the eye carried out on the rabbit proved that components a), b) and c) do not exert irritative action.

Neither sensitization nor intolerance symptoms were observed in skin tests on healthy volunteers.

The compositions of the present invention will be administered topically, in the form of suitable formulations both liquid (such as gel, lotions, milks, emulsions, foams and the like) and solid or semi-solid (such as creams, ointments, lipsticks, and the like). Said formulations will be prepared according to conventional methods, such as those described in "Remington's Pharmaceutical Handbook", Mack Publishing Co, NY, USA, together with suitable excipients, such as emollients, moisturizers, thickening agents, emulsifiers, dyes, flavours and the like.

The invention claimed is:

1. A composition comprising:
    a) 0.1-5% by weight phospholipids complexes of flavanolignanes extracted from *Silybum marianum*,
    b) 0.1-5% by weight phospholipid complexes of standardized extract of *Vitis vinifera*, and
    c) 0.1-5% triterpenes phospholipid complexes of triterpenes extracted from *Glycyrrhiza glabra* in combination with an agent that filters the sun and excipients.

2. The composition according to claim 1, wherein the composition is suitable for topical administration in the form of a liquid.

3. The composition according to claim 1, wherein the composition is suitable for topical administration in the form selected from the group consisting of a gel, lotion, milk, emulsion, and foam.

4. The composition according to claim 1, wherein the composition is suitable for topical administration in the form of a solid or semi-solid.

5. The composition according to claim 1, wherein the compositions are administered topically in a form selected from the group consisting of a cream, ointment, and lipstick.

6. A method of treating skin damage induced by sun radiation in a subject in need thereof comprising administering to said subject an effective amount of the following components:
- a) 0.1-5% by weight of phospholipid complexes with flavanolignanes extracted from *Silybum marianum*,
- b) 0.1-5% by weight of phospholipid complexes of standardized extract of *Vitis vinifera*, and
- c) 0.1-5% phospholipid complexes of triterpenes extracted from *Glycyrrhiza glabra* in combination with an agent that filters the sun and excipients.

7. The method according to claim 6, wherein said composition is administered topically.

* * * * *